US011304816B2

(12) United States Patent
Ponce et al.

(10) Patent No.: US 11,304,816 B2
(45) Date of Patent: Apr. 19, 2022

(54) GLENOID BONE GRAFT RETENTION PLATE

(71) Applicants: Brent Andrew Ponce, Homewood, AL (US); Eugene Willis Brabston, Birmingham, AL (US); Amit Mukesh Momaya, Vestavia, AL (US)

(72) Inventors: Brent Andrew Ponce, Homewood, AL (US); Eugene Willis Brabston, Birmingham, AL (US); Amit Mukesh Momaya, Vestavia, AL (US)

(73) Assignee: Brent Andrew Ponce, Lyons, GA (US)

( * ) Notice: Subject to any disclaimer, the term of this patent is extended or adjusted under 35 U.S.C. 154(b) by 0 days.

(21) Appl. No.: 17/006,370

(22) Filed: Aug. 28, 2020

(65) Prior Publication Data

US 2021/0113343 A1 Apr. 22, 2021

Related U.S. Application Data

(60) Provisional application No. 62/916,135, filed on Oct. 16, 2019.

(51) Int. Cl.
*A61F 2/40* (2006.01)
*A61F 2/30* (2006.01)

(52) U.S. Cl.
CPC .. *A61F 2/4081* (2013.01); *A61F 2002/30461* (2013.01); *A61F 2002/30477* (2013.01);
(Continued)

(58) Field of Classification Search
CPC .......................... A61F 2002/285; A61B 17/82
See application file for complete search history.

(56) References Cited

U.S. PATENT DOCUMENTS

| 722,944 A | 3/1903 | Chautard |
|---|---|---|
| 6,224,602 B1 | 5/2001 | Hayes |

(Continued)

FOREIGN PATENT DOCUMENTS

WO WO-0130252 A1 * 5/2001 ............ A61F 2/0811

OTHER PUBLICATIONS

Translation of WO01/30252A1 retrieved from espacenet on May 6, 2021 (Year: 2021).*

(Continued)

*Primary Examiner* — Megan Y Wolf
(74) *Attorney, Agent, or Firm* — The Gache Law Firm, P.C.; Russell C. Gache

(57) ABSTRACT

A bone graft retention plate for implantation into a human glenoid and provides stabilization and compression of bony graft material is disclosed. The plate includes channels or apertures for suture or polymer retention cerclage that exhibit curved, smooth surfaces within the plate to allow the retention cerclage to pass through the plate while limiting friction and thus protecting the integrity of the retention means. The plate also includes surface features, such as spikes and posts, to provide further stabilization and implantation positioning. The plate features result in the distribution of forces across the surface area of a bone graft and achieve satisfactory compression of the bone graft against the glenoid without using fixation screws. An associated implantation technique uses a cerclage of suture or tape to bind the implant within the glenoid and may be employed in both open and arthroscopic surgical procedures.

21 Claims, 6 Drawing Sheets

(52) U.S. Cl.
CPC ............... *A61F 2002/30578* (2013.01); *A61F 2220/0016* (2013.01); *A61F 2240/001* (2013.01)

(56) References Cited

U.S. PATENT DOCUMENTS

| | | | |
|---|---|---|---|
| 2003/0130694 A1* | 7/2003 | Bojarski | A61F 2/0805 |
| | | | 606/228 |
| 2005/0261775 A1 | 11/2005 | Baum et al. | |
| 2007/0093835 A1* | 4/2007 | Orbay | A61B 17/8061 |
| | | | 606/291 |
| 2009/0318977 A1* | 12/2009 | Di Giacomo | A61B 17/809 |
| | | | 606/286 |
| 2012/0310279 A1* | 12/2012 | Sikora | A61B 17/0401 |
| | | | 606/232 |
| 2013/0238099 A1* | 9/2013 | Hardy | A61F 2/4081 |
| | | | 623/19.11 |
| 2016/0270922 A1 | 9/2016 | Pressacco et al. | |
| 2019/0201206 A1* | 7/2019 | Bettenga | A61F 2/30734 |
| 2019/0254728 A1 | 8/2019 | Skinner | |

OTHER PUBLICATIONS

Definition of "Aperture" retrieved from htttps://www.dictionary.com/browse/aperture on May 6, 2021 (Year: 2021).*

* cited by examiner

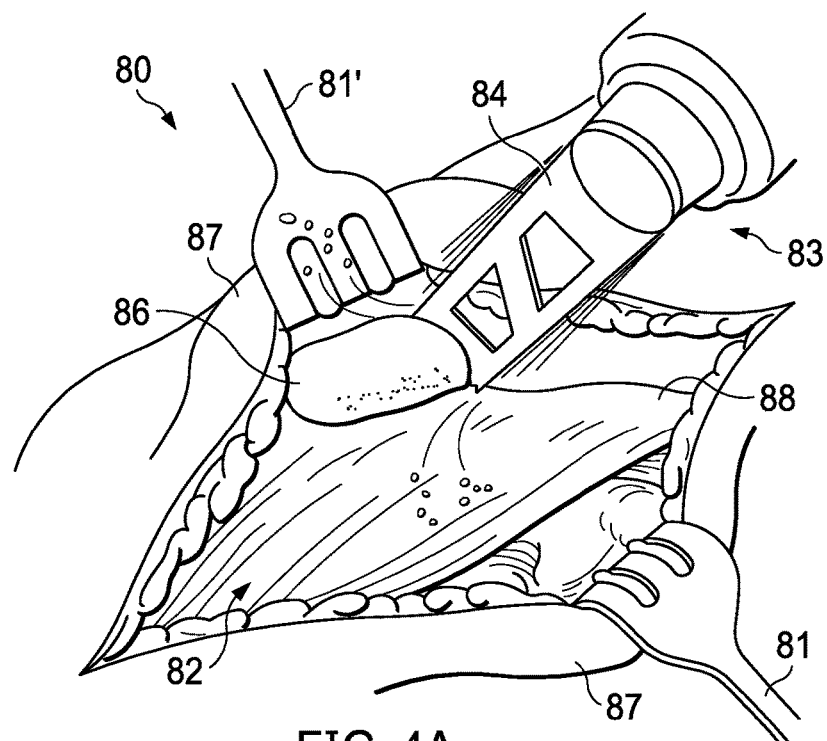
FIG. 4A
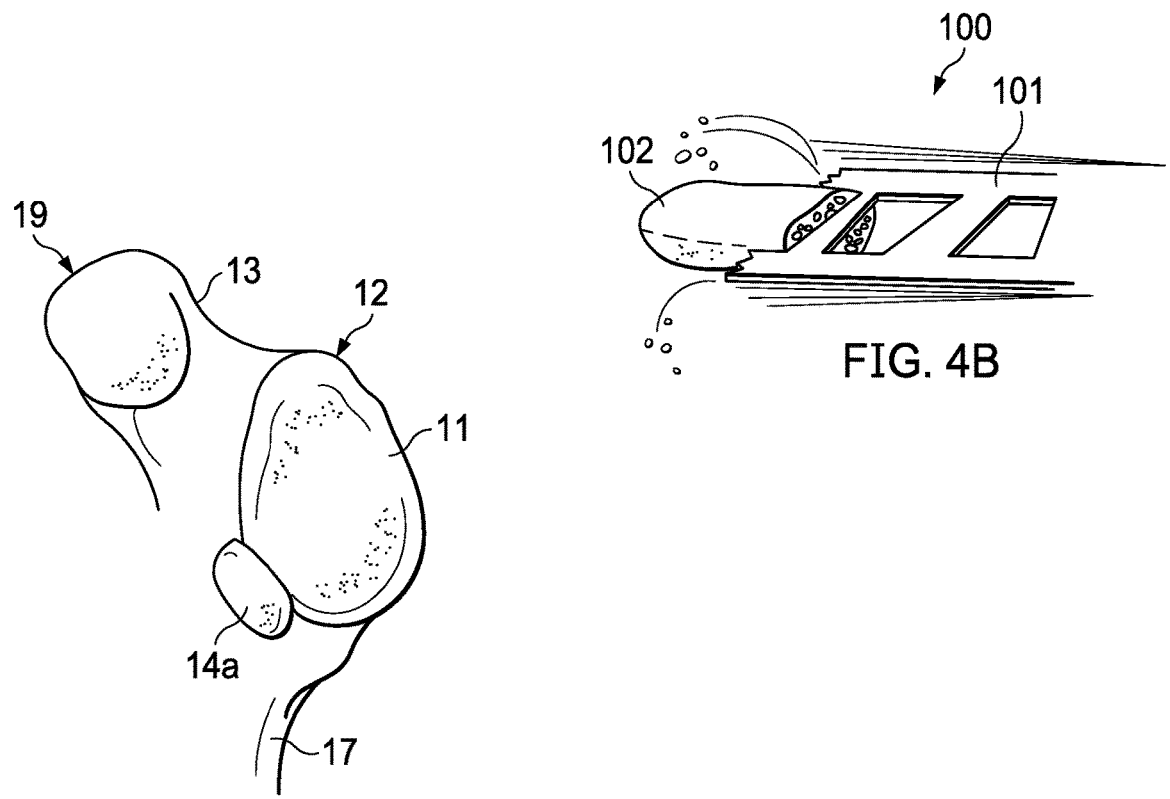
FIG. 4B
FIG. 4C

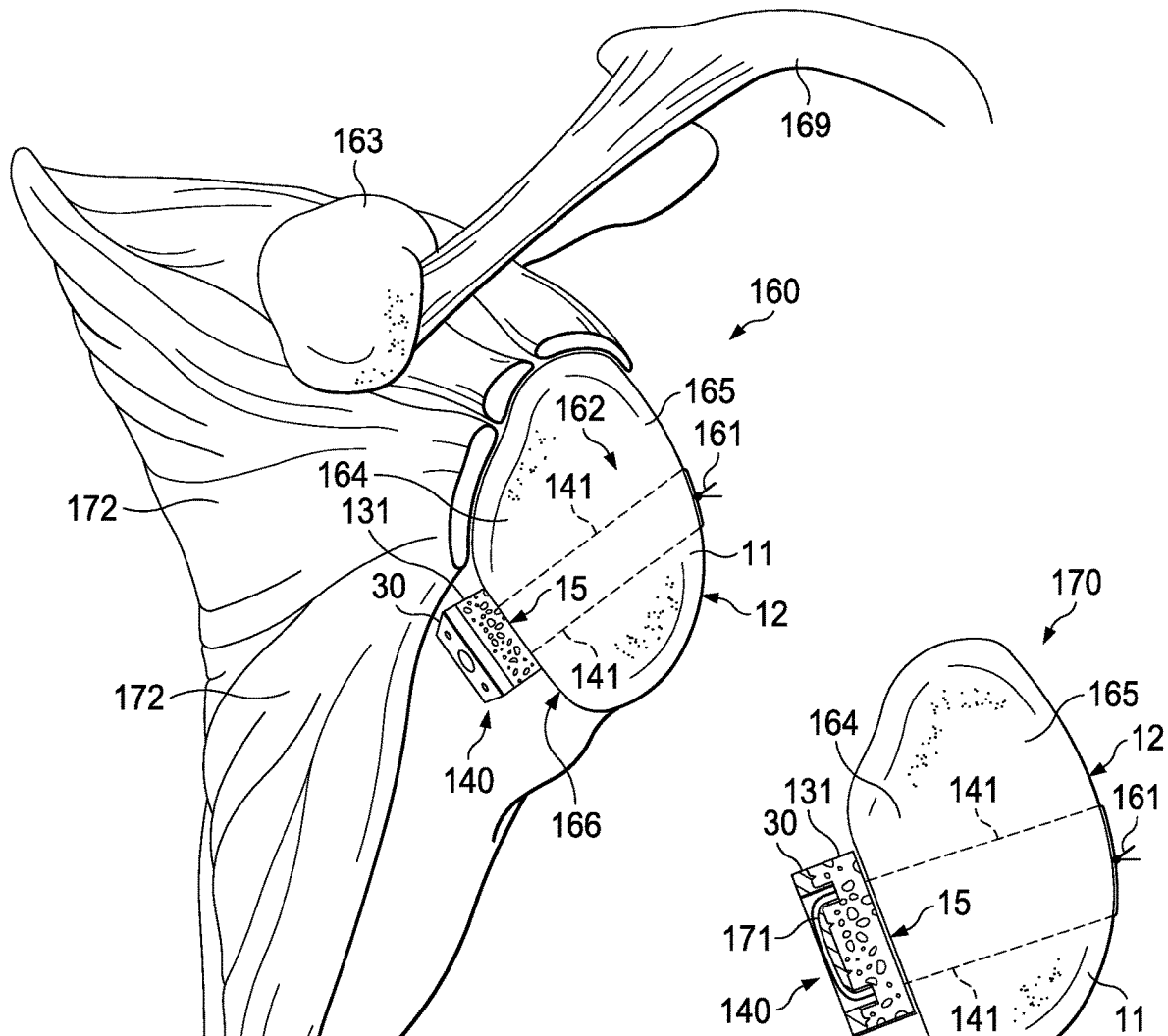
FIG. 6A
FIG. 6B
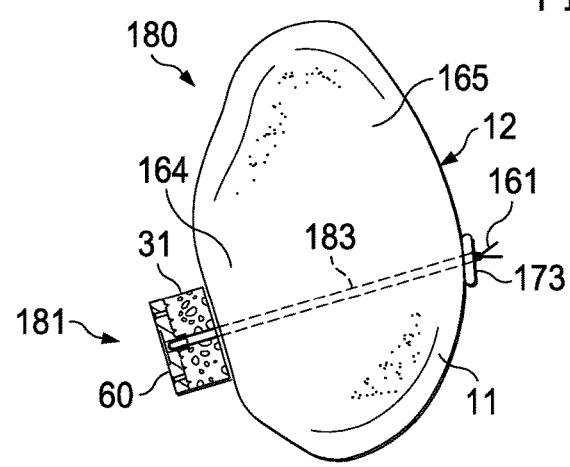
FIG. 6C

GLENOID BONE GRAFT RETENTION PLATE

This application claims the benefit of filing priority under 35 U.S.C. § 119 and 37 C.F.R. § 1.78 of the U.S. Provisional Application Ser. No. 62/916,135 filed Oct. 16, 2019, for a Glenoid Bone Augmentation Plate With Surgical Implantation Technique. All information disclosed in that prior filed application is incorporated herein by reference.

FIELD OF THE INVENTION

The present invention relates generally to surgical instruments. In particular, the invention relates to stabilization plates for human bone. In greater particularity, the invention relates to shoulder socket fixation plates and related surgical installation techniques of such plates along with bone replacement retention strategies.

BACKGROUND OF THE INVENTION

Human shoulders can exhibit instability following trauma from injury or simply through wear. Through a traumatic event, the socket or "glenoid" of the shoulder can have an injury where a piece of bone is either broken off or worn away over time. In the later circumstance, the loss of bone is an attritional process thereby providing no residual bone to reposition into the loss site. With bone loss in the glenoid, a simple soft tissue tightening procedure results in the likelihood of recurrent instability. In response, surgeons usually replace lost bone to reduce the chances of instability re-occurrence.

Various bone transfer procedures to replace lost glenoid bone are known. Most require attaching a free piece of bone or a bone and soft-tissue combination to the targeted glenoid area. The replacement bone or bone and soft-tissue combination, referred to herein as a "graft," are typically attached with screws to compress the graft replacement across the glenoid interface surface to facilitate bony healing. The types of bone graft that have been historically been utilized are an autograft coracoid, an autograft iliac crest, and an allograft distal tibia. As an alternative, an autograft distal clavicle has recently been suggested by some in the industry, but without a broad knowledgebase or well established implementation procedures.

The most common surgical procedure to address bone loss or glenoid fracture was pioneered by French surgeon Dr. Michel Lararjet in 1954 which uses native coracoid in combination with soft tissue attachments to not only add bone to the missing bone site, but also to use the soft tissue to reinforce the stability of the joint. This acts as a bone block which, combined with the transferred muscles acting as a strut, prevents further dislocation of the glenoid joint. The "Latarjet procedure" historically uses screw fixation to compress the coracoid bone to the native glenoid.

The Latarjet and other procedures all use screw fixation to achieve bony compression. However, using screws to compress bone replacement has several disadvantages, and many intraoperative and postoperative complications result from the use of screw fixation. Screw breakage is one possible complication. Exposure of metallic screws to the glenohumeral joint may also result in precipitous and significant cartilage wear. Furthermore, screws of longer than appropriate length may irritate the posterior glenoid soft tissue, and insertion of screws may even break the graft itself. Lastly, the use of screws may require compression rates, depending upon the screw trajectory and path required to satisfactorily stabilize the graft material, that exceed the local tolerances of the bone joint structure in order to properly fix the bone graft into place, or alternatively required compression rates may simply weaken the fixation arrangement necessary to achieve bony union in the graft.

A further complication in using screws is that a patient may exhibit anatomic constraints in the shoulder that may prevent ideal screw placement. For example, the optimal placement of screws may be inhibited by tendons, nerves, and blood vessels and a surgeon may be prevented from performing a relatively minor, less invasive arthroscopic procedure to augment the glenoid with bone in favor of an open surgical procedure, which results in a longer patient recovery time.

As an alternative to screws, the medical industry has attempted to utilize fixation buttons to achieve glenoid bone fixation. However, fixation buttons often cover only a small surface area of the bone block and, generally, are not designed to allow for the free movement of suture cerclage tape or polymer around the graft that is usually required for button fixation. Buttons also lack posts to control the rotation of a fixed bone block and, typically, do not afford satisfactory graft compression as compared to screw fixation techniques.

Therefore, what is needed is device and procedure to achieve bony graft fixation without the use of metallic screws or button fixation.

SUMMARY OF THE INVENTION

It is the object of the present invention to provide a retention plate for implantation into a human glenoid which provides stabilization and compression of two bony surfaces in conjunction with suture or polymer. The plate includes apertures for suture or polymer retention means, and smooth and countered surfaces on the plate allow the retention means to pass through while limiting friction and, thus, protecting the integrity of the retention means. The plate also includes surface features, such as spikes and posts, to provide further stabilization and implantation positioning. The plate features results in the distribution of forces across the surface area of the bone graft and permits the use of suture or polymer to achieve satisfactory compression of the bone graft against the glenoid, while avoiding the use of screws for fixation. An associated implantation technique uses a cerclage of suture or tape to bind the plate within the glenoid and may be employed in both open and arthroscopic surgical procedures.

Other features and objects and advantages of the present invention will become apparent from a reading of the following description as well as a study of the appended drawings.

BRIEF DESCRIPTION OF THE DRAWINGS

An implantable retention plate incorporating the features of the invention is depicted in the attached drawings which form a portion of the disclosure and wherein:

FIG. 4A is a perspective view of a procedure to extract a bone graft;

FIG. 4B is a perspective view of a surgical tool holding the bone graft material;

FIG. 4C is view of FIG. 1A of the glenoid area showing a targeted placement of the bone graft;

FIG. 6A is a human anatomical view of the glenoid with the bone graft plate combination of FIG. 5D in a targeted glenoid position;

FIG. 6B is an isolated view of the glenoid showing a fully implanted bone graft and the retention plate in its final installed position; and, FIG. 6C is an isolated view of the glenoid showing a fully implanted bone graft and a second embodiment of the retention plate in its final installed position.

DESCRIPTION OF THE PREFERRED EMBODIMENTS

Figure 1A:
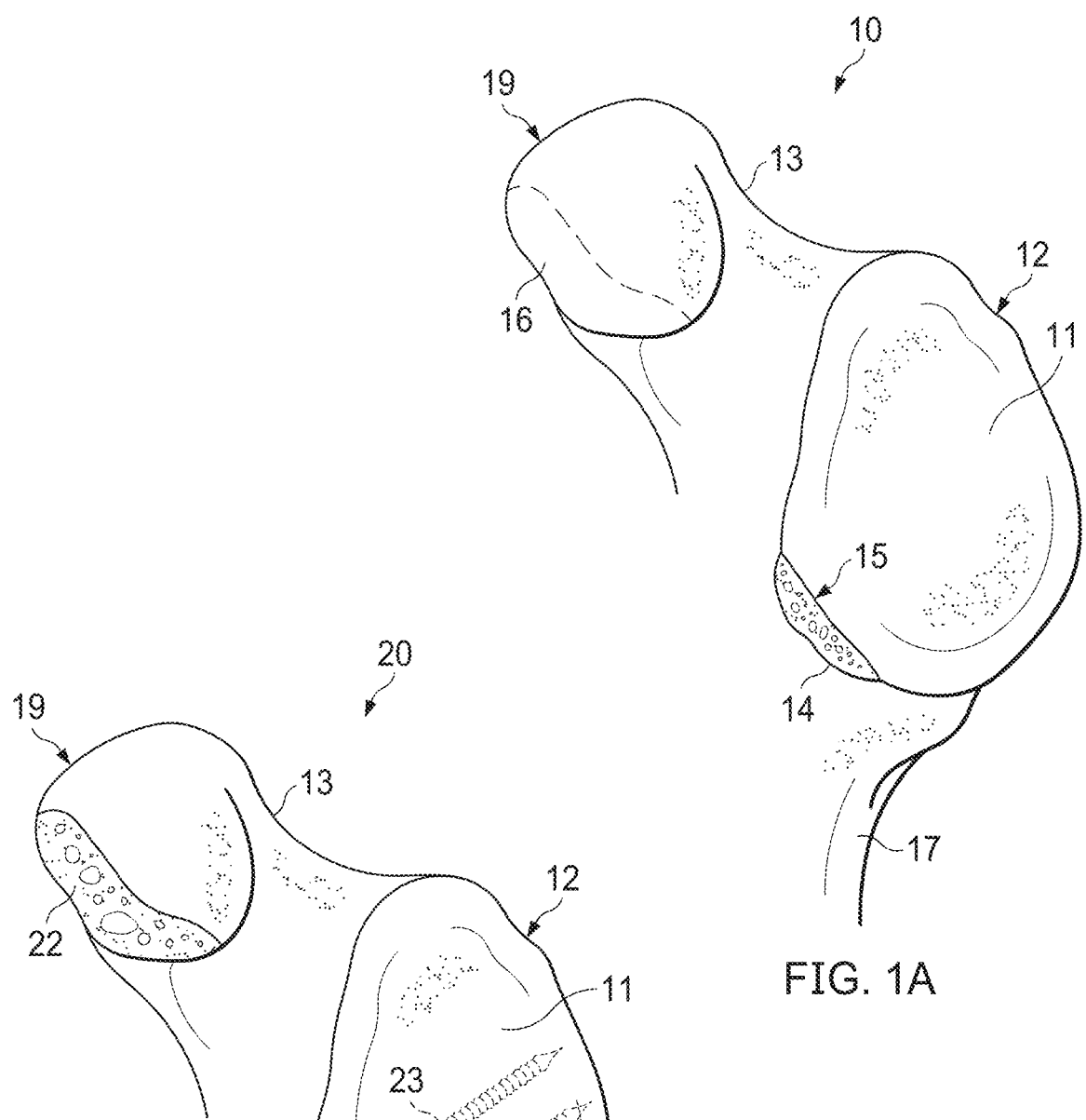
FIG. 1A is a sagittal view of a human left shoulder glenoid area.

Referring to the drawings for a better understanding of the function and structure of the invention, FIG. 1A shows the glenoid area 10 of the body with the surrounding muscle and tendons omitted, and the humerus bone also omitted. The glenoid cavity 11 is circumscribed by a closed, curved periphery of scapula bone 12 onto which a margin of glenoid labrum is attached (not shown). The glenoid cavity 11 is joined to the coracoid 19 via a concave portion of scapula bone 13 and from which an example donor site of bone 16 is potentially extracted, the location of which may vary from patient to patient. The collected bone from site 16 is typically transplanted in a single medical procedure onto a worn or damaged glenoid cavity periphery 14 to form a graft 15 that buttresses the glenoid. A lower portion of the scapula 17 supports both the glenoid cavity 11, the coracoid 19, and the newly transplanted graft.

Figure 1B:
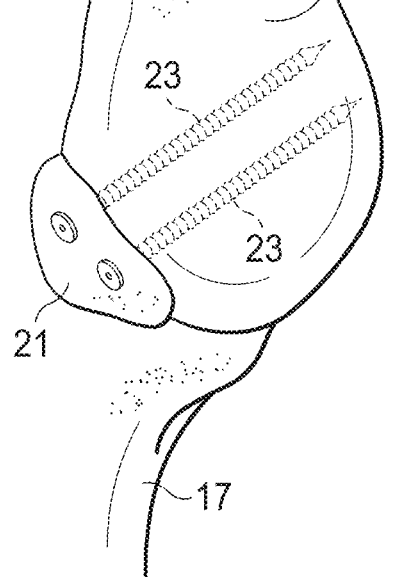
FIG. 1B is the view of glenoid of FIG. 1A showing the traditional use of fixation screws to fix a bone graft onto the glenoid.

FIG. 1B shows a traditional fixation method for the glenoid area 10 in which the bone collected from the extraction donor site 22 is positioned onto the worn site 14 as a graft 21. One or more fixation screws 23 penetrate the graft 21 and the supporting scapula bone 17 below the glenoid cavity surface as shown to hold the graft in place.

FIGS. 2A-2D show different views of one embodiment of the invention. Implantable plate 30 includes a top surface 38 having a generally rectangular shape with curved outer sidewall 51 depending downward from top surface 38. Plate body 32 will typically have a length x (39) of approximately 15 mm-20 mm and a width y (41) of approximately 10 mm, but as may be understood plates of various lengths x and widths y would be sized to accommodate a wide range of patient glenoid shapes and sizes. Body 32 includes a recessed circular portion 34 formed in surface 38 which is bisected by recessed slot 33 connecting a pair of circular passageways 46,46.' Recess 34 allows for the use of a surgical temp or a plate holder (not shown) to assist in the positioning of the plate 30 during implantation. Body 32 may be made of any suitably ridged material to support bone graft compression and fixation, such as, for example, aluminum, stainless steel, high grade polymer, titanium, titanium alloy, PEEK (poly-ether-ether ketone), etc., as long as the material used is suitable for long-term implantation within a human body. Slot 33 and passageways 46,46' are formed as an interior, integral hollow space 44 with each passageway 46,46' providing an opening or aperture from the top surface 38 to lower surface 35 and extending through lower openings 47,47', which depend downward from lower surface 35 to form two positioning posts. A pair of small suture holes 42,42' are positioned toward left and right peripheral margins of body 32 and provide angled, suture fixation points from top surface 38 to the sides 36 of body 32, and supply supplemental fixation points during a medical procedure. A plurality of sharp points or spikes 49 extend downward from lower surface 35 by a distance of approximately 3 mm and are positioned to provide provisional gripping to an adjacent bone graft. The present embodiment utilizes 6 spikes, but as may be understood the number and positioning of the spikes 49 will vary with the size and configuration of the plate 30 responsive to a patients glenoid size and shape. The two passageways 46,46' are spaced apart approximately 10 mm and together with integral hollow space 44 are arranged to allow for positioning control of plate 30 during implantation against glenoid cavity 11 with sutures. As shown, the passageways 46,46' and slot 33 are integrally curved, avoiding any sharp turns, to facilitate the distribution of downward force applied to the bone graft material by a fixation suture in a nonbinding or slidable manner.

A second embodiment of the invention may be seen in FIGS. 3A-3D. Body 32 has dimensions similar to the plate shown in FIG. 2A and also has a generally rectangular body 32 as before. However, second embodiment 60 includes a central recessed portion 71 formed in body 32, having a lowered uniform surface 72 that defines a central passageway 73, instead of an integral slot connecting two passageways as in embodiment 30. Central passageway 73 is bisected into a two opposing channels or passageways starting at a smooth, downwardly curved median 66 extending from recessed surface 72 through to lower portion 67. A pair of alternative suture passageways 65,65' are centrally disposed on surface 38 and positioned in line with the two exterior small suture apertures 31,31' and central passageway 73, and extend through body 32 from upper surface 38 to lower surface 35. The upper portion of passageways 65,65' are chamfered at their juncture with upper surface 38 to allow for the optional use of fixation screws (not shown) to be used in passageways 65,65' in a manner that results in the tops of each screw to be flush with or below surface 38.

Figure 2A:
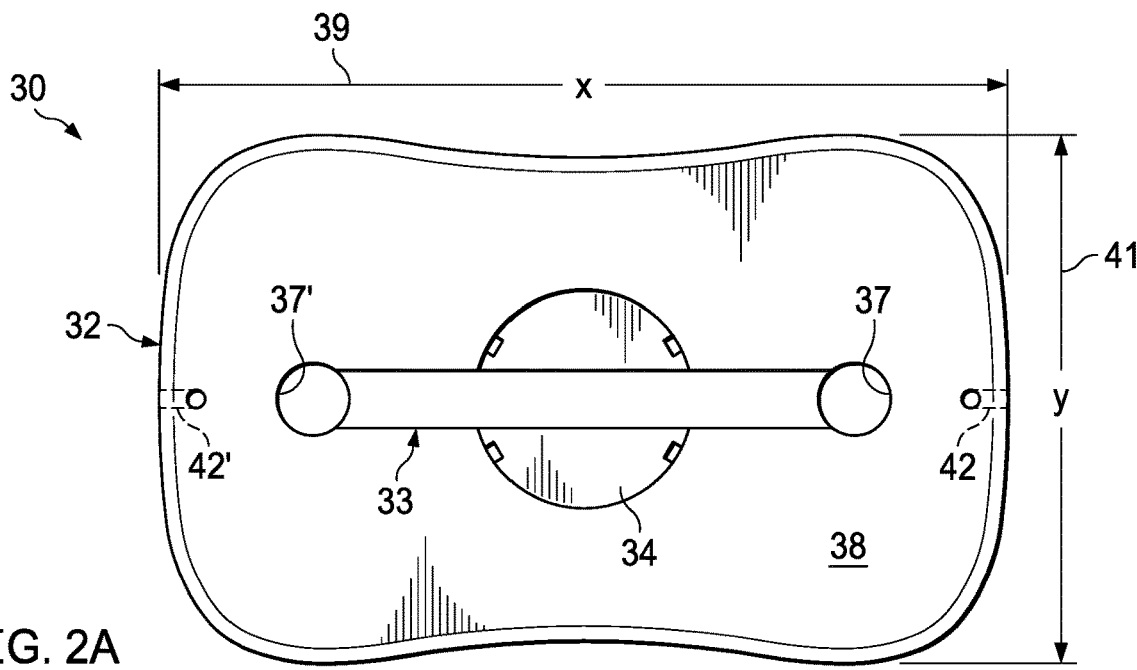
FIG. 2A is a plan view of the proposed implantable retention plate.
Figure 2B:
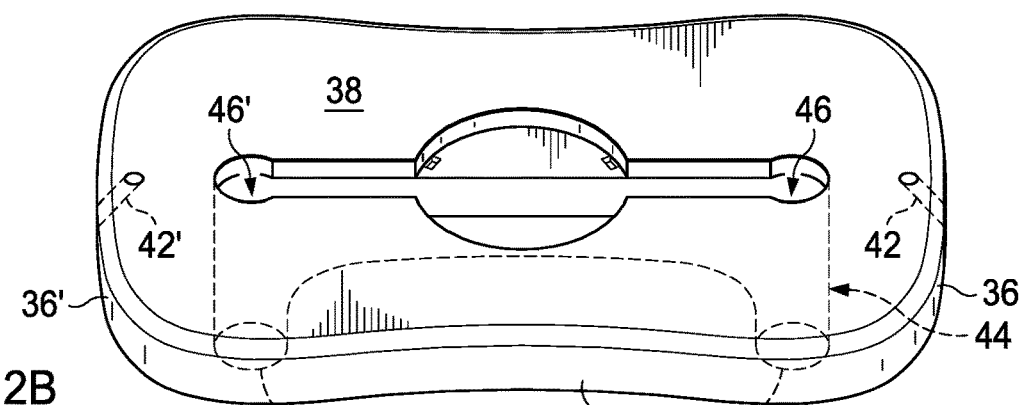
FIG. 2B is a top perspective view of the plate.
Figure 2C:
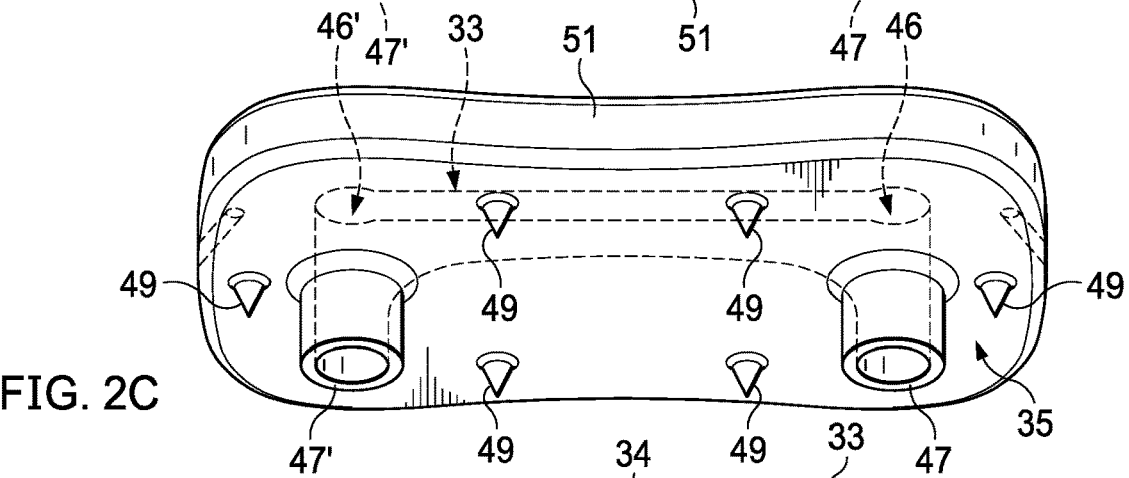
FIG. 2C is a bottom perspective view of the plate.
Figure 2D:
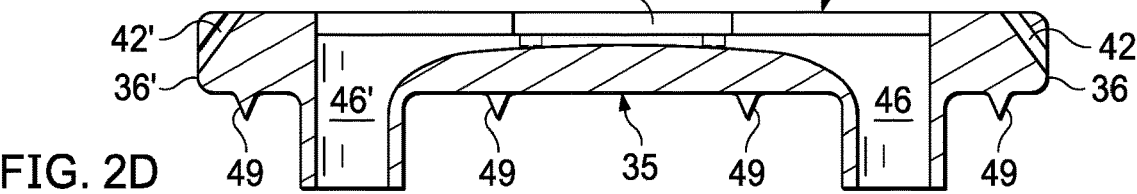
FIG. 2D is a side elevational view of the plate.
Figure 3A:
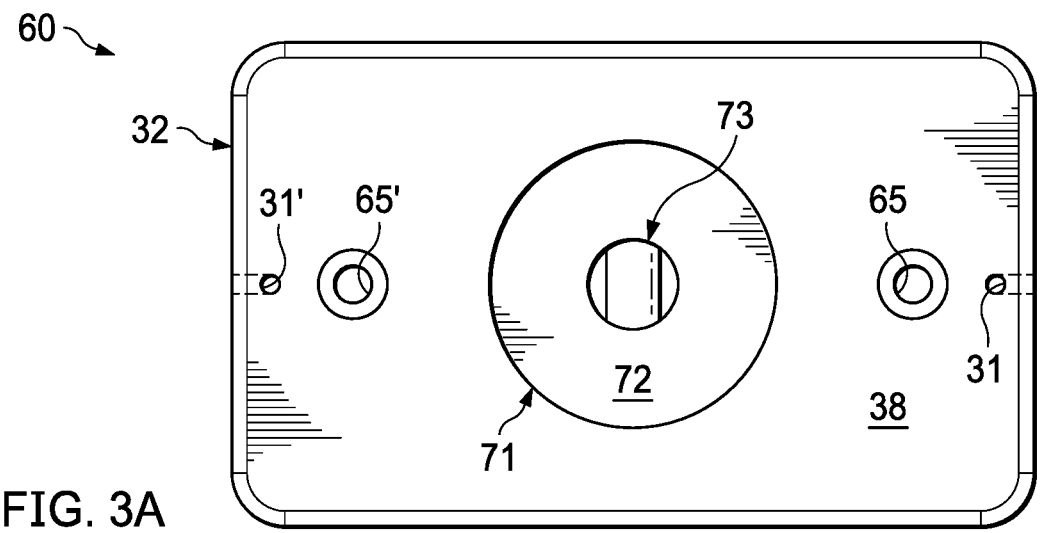
FIG. 3A is a plan view of a second embodiment of the implantable retention plate.
Figure 3B:
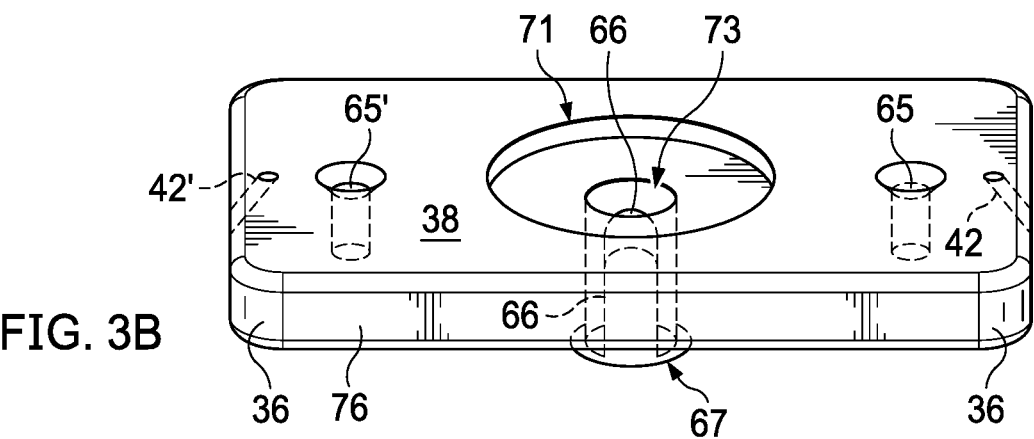
FIG. 3B is a top perspective view of a second embodiment of the plate.
Figure 3C:
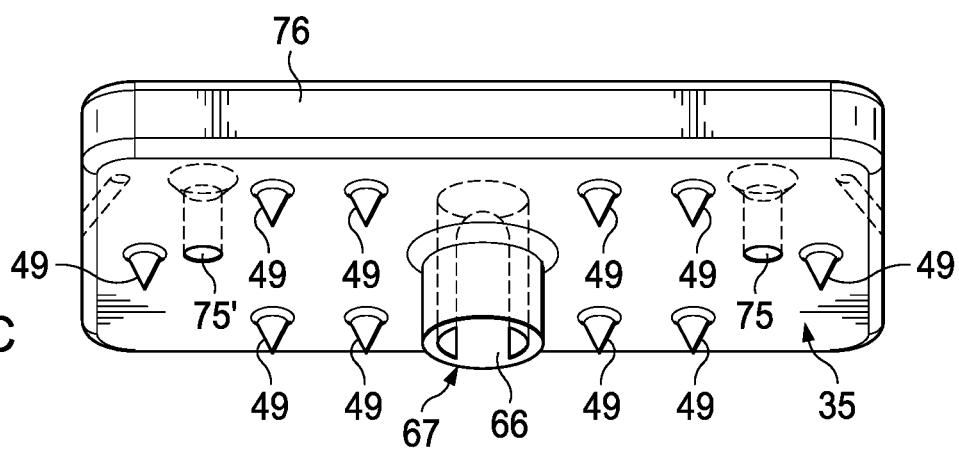
FIG. 3C is a bottom perspective view of a second embodiment of the plate.
Figure 3D:
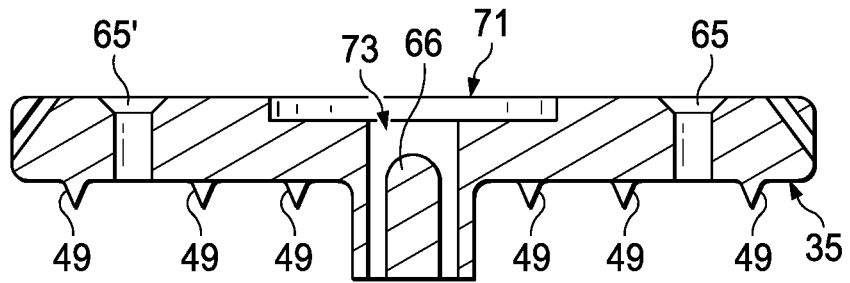
FIG. 3D is a side elevational view of a second embodiment of the plate.

Referring now to FIGS. 4A-4C and FIGS. 5A-5D, a series of steps are shown to illustrate extraction of bone material and preparation of that material for use with the retention plate 30 shown in FIG. 2A. As will be understood, the steps shown can be adapted to be used with plate 60 shown in FIG. 3A. As seen in FIG. 4A, bone graft material may be harvested in a standard manner using standard techniques and may be obtained from the distal clavicle 80, from the coracoid area shown in FIG. 1A, or from other suitable donor sites in the patient's body. A transverse or longitudinal incision 82 is made over a the clavicle region 87 of the patient, spreaders 81,81' used to enlarge the opening, and the deltotrapezial layer 88 exposed. The acromioclavicular capsule is then incised and the distal clavicle cut with a surgical saw and an osteotome 83 having a sharp, beveled tip 84 (101 in FIG. 4B) used to collect bone graft material. Typically, bone material 102 is a minimum of 20 mm superior to inferior, 10 mm medial to lateral, and 10 mm anterior to posterior, as shown 100. The amount and density of the material 102 must comport with the target site 14a so that the repair or augmentation goals of the glenoid are 11 satisfied.

Figure 5A:
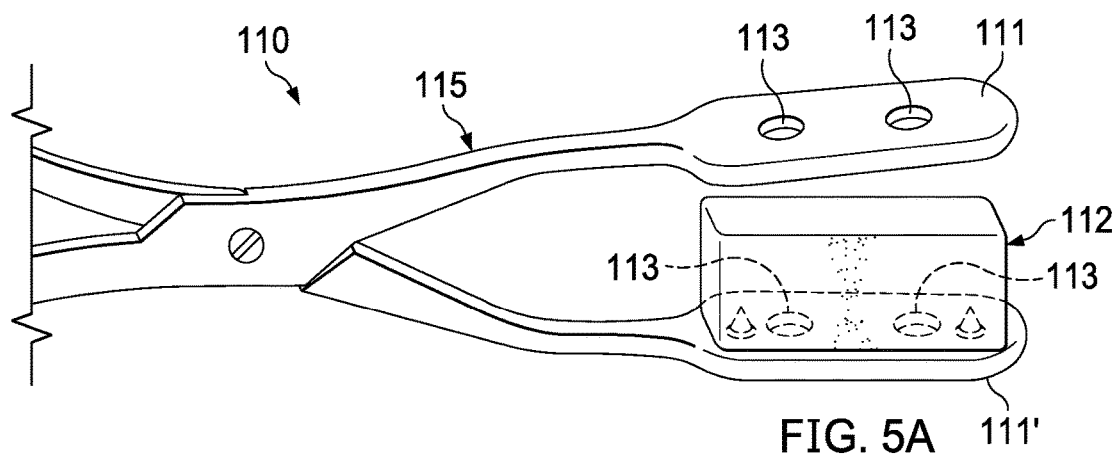
FIG. 5A is a perspective view of a surgical tool holding the bone graft.
Figure 5B:
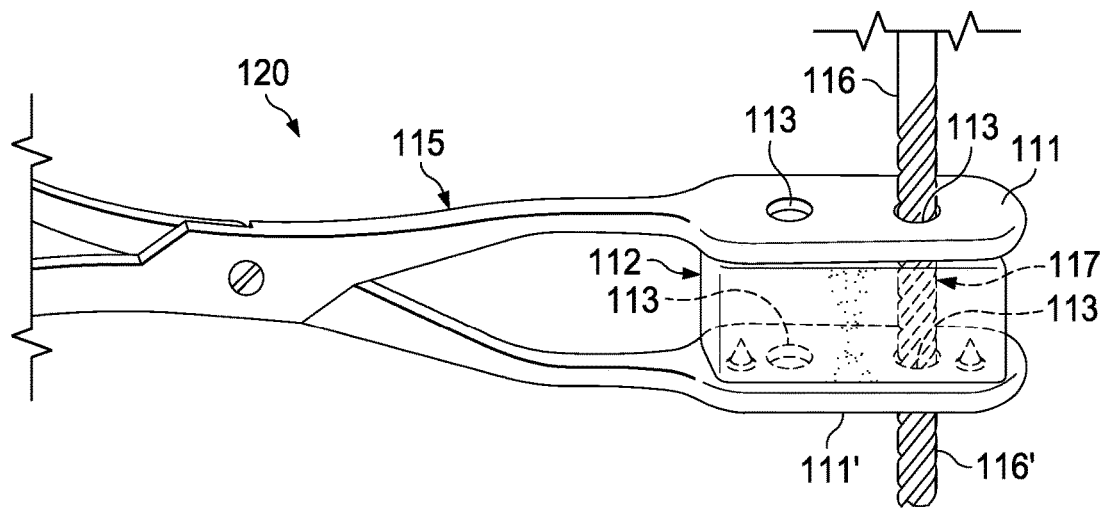
FIG. 5B is a perspective view of the tool holding the bone graft with a drill bit positioned to create two passageways in the bone graft.
Figure 5C:
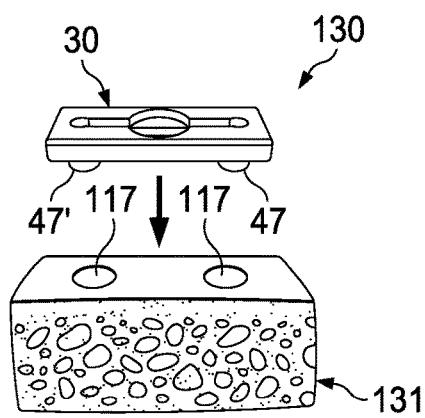
FIG. 5C is a perspective view of the bone graft of FIG. 5B having the plate about to be positioned on the graft.
Figure 5D:
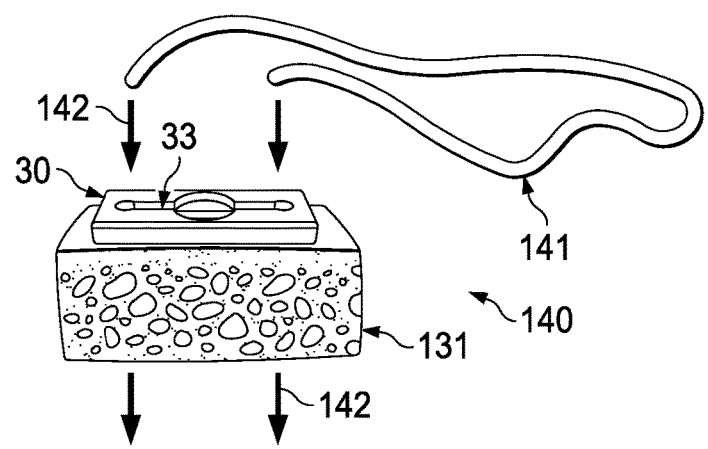
FIG. 5D is a perspective view of the bone graft combined with the plate showing the placement of the sutures relative to the plate.

After the graft material 102 is obtained, a bone clamp 115 is used to stabilize 110 the graft material 112 for additional preparation. The clamp 115 includes on each side 111,111' a pair of opposing apertures 113 sized for the passage of an appropriate drilling bit 116. The clamp 115 is used to compact and form the material 112 into the size and shape needed, and one or two holes drilled 117 through the material a suitable distance apart from each other to match the passageways present in a selected retention plate. Typically, a single hole is drilled for small grafts while two holes are drilled for standard sized grafts. As shown in FIG. 5C, the retention plate 30, for example, is pressed 130 onto the formed bone graft material 131 such that the passageways 46,46' are aligned with and engaged within the drilled holes 117 starting with lower post portions 47,47' that assist with positioning. Once fully engaged, a shuttling loop 141 (FIG. 5D) is placed from deep to superficial in one hole and superficial to deep in the other hole 142. An additional suture may be placed through the inferior drill holes 42,42' (See FIGS. 2A-2B) as a traction suture (not shown).

Referring now to FIG. 6A-6B, an open or arthroscopic procedure is used after the bone graft material 131 and retention plate 30 are prepared to administer the graft combination 140 to the targeted glenoid site 15. For example, arthroscopic portals may be created to enter the glenohumeral joint 160 so that in an augmentation requirement due to anterior glenoid bone loss is confirmed, followed by biologic preparation to receive the bone graft/retention plate combination 140. A spinal needle or other rigid instrument is used to access the trajectory of the drill tunnels 141 and an incision made with blunt spreading through the deltoid 164 and infraspinatus tissue 172. Contact with the posterior glenoid 165 may then be done. A cannulated drill guide is introduced posteriorly and used to drill two parallel holes 141 to the desired location target location 15. A k-wire 171 is placed into position and then a cannulated drill is placed over the wire and repeated for the second drill hole 141.

A shuttling suture is then placed through the cannulated drill holes and pulled through the anterior glenoid 166. The cannulated drill guide is removed and the ends of the sutures are secured. The two drill holes 141 are assessed by viewing from an anterior viewing portal to make sure that there is at least 5 mm of bone present between both of the two drill holes and the face of the glenoid 162. After satisfactory placement, a camera is placed posteriorly again, and the suture strands are used to pull suture tape or polymer through passages 46,46' of the plate 30 in a cerclage arrangement for fixation of the retention plate 30 and graft material 131 combination against the anterior glenoid 166. Each suture in the glenoid 12 is pulled, thereby pulling the two ends of the suture tape or polymer around the combination 140. Using a single traction suture, the combination 140 is then pulled through the anterior soft tissue cannula into the joint, and the two limbs of the single cerclage suture tape or polymer pulled to remove any slack or extraneous suture material. Once the bone graft is positioned next to the native glenoid, traction is applied to the ends of the sutures to allow for proper bone contact, and a suture tape tensioning device advanced from the posterior incision such that both ends of the single limb of suture are placed into the tensioning device. The two limbs of the suture are then fed into each other or spliced to allow for fixation, and the tensioning device engaged with direct visualization from the anterior portal. Once final tightening is done, the posterior suture is tied 161 and a probe used to assess the stability of the arrangement. Additional anterior labral repair may be performed superior and inferior to the retention plate/bone graft combination 140 in a standard fashion. FIG. 6B shows how the final arrangement should appear. FIG. 6C shows how a final arrangement using the above described procedure will appear using the retention plate 60 shown in FIG. 3A. As shown, a fixation button 173 may be utilized to secure the suture tape through passageway 183.

While I have shown my invention in one form, it will be obvious to those skilled in the art that it is not so limited but is susceptible of various changes and modifications without departing from the spirit thereof. For example, the invention may be employed in various techniques to achieve reconstruction goals in which bone graft material must be fixed in place within a human body. For example, the invention may be used for bone block transplantation, such as in Latarjet procedures, iliac crest transfers, distal clavicle transfers, allograft transfers, bone fusions, osteotomies, and fracture fixation procedures. The invention may generally be utilized for small joint surgeries as well. The inventors further contemplate that the herein described devices and procedures may be applied to mammals of various types, in addition to human patients.

Having set forth the nature of the invention, what is claimed is:

1. A bone graft retention plate for compressing bone graft material against a target glenoid area, comprising:
    a. a rigid plate body having an upper and lower surface, said rigid plate body having a generally rectangular shape;
    b. a recessed portion in said upper surface defining a suture anchoring path disposed generally within the center of said rigid plate body, wherein said suture anchoring path includes two separate downward descending passageways extending from said upper surface to said lower surface;
    c. wherein said two separate downward descending passageways form in said lower surface at least one post depending downward from said lower surface for positioning said rigid plate body onto said bone graft material;
    d. an anchoring suture positioned through said suture anchoring path and adapted to form a cerclage around a portion of human bone for securing said retention plate and bone graft material against said glenoid area; and
    e. wherein said rigid plate body further defines a first recessed portion in said upper surface configured to receive a tool and positioned substantially at the center of said upper surface, wherein said first recessed portion is connected to said two separate downward descending passageways, and wherein said two separate downward descending passageways are connected within said rigid plate body via a slot recessed in said upper surface.

2. The retention plate as recited in claim 1, wherein said two separate downward descending passageways form two downward depending hollow posts for positioning said retention plate onto said bone graft material, and wherein said two downward depending hollow posts extend downward from said lower surface of said rigid plate body at right angles relative to said lower surface, wherein said anchoring suture is positioned through said two separate downward descending passageways and through each said downward depending hollow posts.

3. The retention plate as recited in claim 2, further comprising a plurality of conical spikes depending downward from said lower surface for provisional retention of said bone graft material against said retention plate.

4. The retention plate as recited in claim 3, wherein said rigid plate body further defines at least two apertures disposed within said upper surface, each adapted for receiving a fixation screw through said upper surface and extending through said rigid plate body, wherein each screw is adapted for anchoring said retention plate against said glenoid area.

5. The retention plate as recited in claim 1, wherein said two separate downward descending passageways comprise a single central aperture in said rigid plate body having a median divider extending through the center of said central aperture to form two suture channels.

6. The retention plate as recited in claim 5, wherein said two separate downward descending passageways present solely smooth curved surfaces to said anchoring suture positioned therein such that said anchoring suture slides freely within said retention plate.

7. The retention plate as recited in claim 6, further comprising a plurality of conical spikes surrounding said at least one post depending from said lower surface for provisional retention of said bone graft material against said retention plate.

8. The retention plate as recited in claim 1, further comprising two downward depending hollow posts parallel to one another and perpendicular to said lower surface of said rigid plate body.

9. The retention plate as recited in claim 8, further comprising a plurality of conical spikes depending downward from said lower surface and surrounding each of said downward depending hollow posts for provisional retention of said bone graft material against said retention plate.

10. The retention plate as recited in claim 9, further including upstanding side walls connecting said upper and lower surfaces, said upper surface including a peripheral margin extending inward from a periphery of said upper surface, wherein said upper surface and side walls define a least two suture apertures connecting said upper surface and said side walls within the peripheral margin of said upper surface.

11. A bone graft retention plate, comprising:
 a. a rigid plate body having upper and lower surfaces and bounded by generally perpendicular sides;
 b. a pair of smooth walled anchor passageways disposed within said rigid plate body and connecting said upper and lower surfaces, said pair of smooth walled anchor passageways including lower portions depending downward from said lower surface to form at least one hollow positioning post;
 c. an anchoring suture positioned within said pair of smooth walled anchor passageways and configured to form a cerclage within a portion of glenoid bone;
 d. wherein said air of smooth walled anchor passageways are configured to reduce friction of said anchoring suture when pulled therethrough;
 e. a plurality of spikes depending downward from said lower surface of said rigid plate body for provisional fixation against a shaped mass of glenoid suitable bone graft material; and
 f. wherein said rigid plate body further defines a first recessed portion in said upper surface configured to receive a tool and positioned substantially at the center of said upper surface, wherein said first recessed portion is connected to said pair of smooth walled anchor passageways, and wherein said pair of smooth walled anchor passageways are connected within said rigid plate body via a slot recessed in said upper surface.

12. The retention plate as recited in claim 11, wherein said at least one hollow positioning post forms a 90 degree angle with said lower surface of said rigid plate body, and wherein said pair of smooth walled anchor passageways comprise a single central aperture in said rigid plate body having a median divider extending through the center of said single central aperture to form two suture channels.

13. The retention plate as recited in claim 12, wherein said pair of smooth walled anchor passageways are formed with smooth inner surfaces such that said anchoring suture slides freely within said pair of smooth walled anchor passageways, and wherein said plurality of spikes are conically shaped.

14. The retention plate as recited in claim 12, wherein said median divider is positioned below said first recessed portion formed in said upper surface and extends throughout said entire at least one hollow positioning post depending from said lower surface such that said pair of smooth walled anchor passageways are isolated from one another along the entire length of said at least one hollow positioning post.

15. The retention plate as recited in claim 11, wherein said pair of smooth walled anchor passageways depend downward from said lower surface to form two downward depending hollow positioning posts each forming a 90 degree angle relative to said lower surface of said rigid plate body for positioning said retention plate onto said bone graft material.

16. A procedure for fixing a shaped mass of glenoid suitable bone graft material to augment the glenoid area of a human body, comprising the steps of:
 a. obtaining suitable amount of bone graft material to augment said glenoid area;
 b. compressing said bone graft material with a bone clamp;
 c. pressing the compressed bone graft material against the retention plate recited in claim 1;
 d. drilling at least one aperture through said bone graft material aligned with two downward descending passageways in the retention plate;
 e. positioning the combination of the bone graft material and the retention plate on a targeted glenoid augmentation area through a medical procedure; and,
 f. drilling at least one tunnel through bone supporting said targeted glenoid augmentation area and threading the anchoring suture through said combination of the bone graft material and the retention plate in a cerclage arrangement such that said combination of the bone graft material and the retention plate are compressed against said targeted glenoid area.

17. The procedure as recited in claim 16, wherein said step of drilling at least one tunnel through bone supporting said targeted glenoid augmentation area comprises drilling two tunnels, and wherein each tunnel receives the anchoring suture in said cerclage arrangement.

18. The procedure as recited in claim 17, wherein said step of obtaining suitable amount of bone graft material comprises the step of harvesting donor bone material from said same human body.

19. The procedure as recited in claim 18, further including the step of using an anchoring button in said cerclage arrangement positioned on bone supporting said glenoid area.

20. The procedure as recited in claim 18, wherein said step of drilling at least one aperture through said bone graft material comprising drilling a plurality of apertures, each aperture aligned with a unique passageway present in said retention plate and each aperture receiving a downward depending hollow anchoring post formed on the lower surface of said retention plate at a right angle thereof.

21. The procedure as recited in claim 20, further including the step of using an anchoring button in said cerclage arrangement positioned on bone supporting said glenoid area.

* * * * *